United States Patent
Lu et al.

(10) Patent No.: US 8,932,824 B2
(45) Date of Patent: *Jan. 13, 2015

(54) METHOD OF DETECTING CANCER USING DELTA-CATENIN

(75) Inventors: Qun Lu, Greenville, NC (US); Yan-hua Chen, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/251,481

(22) Filed: Oct. 3, 2011

(65) Prior Publication Data

US 2012/0100998 A1    Apr. 26, 2012

Related U.S. Application Data (63) Continuation of application No. 12/238,539, filed on Sep. 26, 2008, now Pat. No. 8,058,020, which is a continuation of application No. 10/872,692, filed on Jun. 21, 2004, now Pat. No. 7,445,906.

(60) Provisional application No. 60/483,666, filed on Jun. 30, 2003.

(51) Int. Cl.
  *G01N 33/574*    (2006.01)

(52) U.S. Cl.
  CPC ........ *G01N 33/57434* (2013.01); *G01N 33/574* (2013.01)
  USPC .......................................... 435/7.23; 435/7.1

(58) Field of Classification Search
  None
  See application file for complete search history.

(56) References Cited

U.S. PATENT DOCUMENTS 6,258,929 B1    7/2001  Kosik et al.

OTHER PUBLICATIONS

Burger et al (Int J. Can, 100: 228-237, 2002, IDS, Jan. 6, 2012, No. 1.*
Lu et al The Prostate, 69:411-418, 2009, DS, Jan. 6, 2012, No. 3.*
Zhang et al J Pathology, 222:76-88, 2010, DS, Jan. 6, 2012, No. 2.*
Burger MJ et al. Int J. Cancer. 100:228-237, 2002, IDS, p. 3, Sep. 26, 2008.
Zhang J-Y et al. Delta-catenin promotes malignant phenotype of non-small cell lung cancer by con-competitive binding to E-cadherin with p120ctn in cytoplasm. Journal of Pathology. 2010; 222: 76-88.
Lu Q et al. Identification of extracellular delta-catenin accumulation for prostate cancer detection. The Prostate. 2009; 60: 411-418.
MeSH word search result, 2010.
S. Kirchheimer, High PSA Level? Check it Again (May 27, 2003).
National Cancer Institute, Fact Sheet: The Prostate-Specific Antigen (PSA) Test: Questions and Answers (Aug. 21, 2007).
A Krist et al., Should you get a PSA test? A Patient Doctor Decision (2007).
W. Catalona, PSA Screening: It's a Must (2007).
International Search Report and Written Opinion for PCT Application No. PCT/US2004/19895, Mailed May 2, 2006.
Burger, Michelle Jane et al. (2002) "Expression Analysis of δ-Catenin and Prostate-Specific Membrane Antigen: Their Potential as Diagnostic Markers for Prostate Cancer." *Int. J. Cancer*: 100, 228-237.
Kim, Kwonseop et al. (2002) "Dendrite-like Process Formation and Cytoskeletal Remodeling Regulated by δ-Catenin Expression." *Experimental Cell Research*, 275, 171-184.
Lu, Q. et al. (2002) "Brain Armadillo Protein δ-Catenin Interacts with Abl Tyrosine Kinase and Modulates Cellular Morphogenesis in Response to Growth Factors" *Journal of Neuroscience Research*: 67, 618-624.
MeSH word search result. delta catenin. Printed Jan. 16, 2008.
Thoreson MA et al. Altered expression of the catenin p120 in human cancer: implications for tumor progression. Differentiation. Dec. 2002; 70(9-10): 583-589. Abstract.
Skoudy A et al. p120-catenin expression in human colorectal cancer. Int J Cancer. Sep. 27, 1996; 68(1): 14-20. Abstract.
Dillon DA et al. The expression of p120ctn protein in breast cancer is independent of alpha- and beta-catenin and E-cadherin. Am J Pathol. Jan. 1998; 1521(1): 75-82. Abstract.

* cited by examiner

*Primary Examiner* — Lei Yao
(74) *Attorney, Agent, or Firm* — Myers Bigel Sibley & Sajovec, P.A.

(57)    ABSTRACT

The present invention provides a method for detecting or screening for the presence of cancer in a subject. The method comprises obtaining, providing or collecting a tissue or fluid sample (such as a urine sample) from said subject, and then determining the presence or absence of delta-catenin in said sample, or increased levels of delta-catenin in said sample as compared to a normal or control subject. The presence of delta-catenin in said sample, or increased levels of delta-catenin in said sample, indicating said subject is afflicted with or at least at risk of developing cancer.

18 Claims, 9 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: RT-PCT primer

<400> SEQUENCE: 1
tactccgcaa gacgactgac c                                    21

```
<210> SEQ ID NO 2
<211> LENGTH: 24
<212> TYPE: DNA
<213> ORGANISM: Artificial
<220> FEATURE:
<223> OTHER INFORMATION: RT-PCT primer

<400> SEQUENCE: 2
ccatcacact ctctcatcct tctg                                          24
```

METHOD OF DETECTING CANCER USING DELTA-CATENIN

RELATED APPLICATIONS

This application claims priority to and is a continuation of U.S. patent application Ser. No. 12/238,539, filed Sep. 26, 2008, now U.S. Pat. No. 8,058,020, which is a continuation of U.S. patent application Ser. No. 10/872,692, filed Jun. 21, 2004, now U.S. Pat. No. 7,445,906 and also claims the benefit of U.S. Provisional Patent Application Ser. No. 60/483,666, filed Jun. 30, 2003, the disclosure of each of which is incorporated by reference herein in its entirety.

BACKGROUND OF THE INVENTION

Prostate cancer is a major cause of death among men in Western countries. The current protocol for detection of this cancer involves testing for prostate-specific antigen (PSA) levels. If PSA levels are found to be high (4 ng/ml), a tissue biopsy is performed. Unfortunately, PSA testing is limited by the fact that it lacks sensitivity and it does not distinguish between prostate cancer and benign prostate hyperplasia. As a result, many men either are not identified as having the disease or because of false positive tests are subjected to the invasive tissue biopsies when they do not have the disease. A much more specific and less invasive diagnostic test is needed for early detection of this disease.

Delta-catenin presents itself as an improved alternative to the PSA/biopsy tests currently utilized for prostate cancer detection. Delta catenin was first identified and patented (U.S. Pat. No. 6,258,929) as a neurospecific protein, alternatively named ALARM. At the time, the protein was believed to be expressed almost exclusively in brain tissue. However, Burger, et al. (*Int. J. Cancer* 100, 228-237 (2002)) subsequently found the messenger RNA for delta-catenin to be expressed in prostate cancer tumors with the delta-catenin transcripts being localized to the glandular secretory cells. Unlike PSA, delta-catenin was capable of distinguishing between prostate cancer and benign prostate hyperplasia. Burger et al. noted a possible diagnostic role for delta-catenin in prostate cancer detection. However, they also pointed out that a significant difficulty remained in development of this tool since delta-catenin had only been detected in glandular secretory epithelial cells in prostate tissues and had not been found in prostate stroma or bodily fluids, such as serum or urine.

SUMMARY OF THE INVENTION

The present invention shows that delta-catenin mRNA and protein are expressed not only in prostate cancer tissues but also in many other cancer types. For example, in esophageal cancer, delta-catenin expression, like in prostate cancer, increases with the increasing tumor grade. Thus, its usefulness may extend beyond detection of prostate cancer. Moreover, it has now been found that when over-expressed, delta-catenin can be detected not only in the affected epithelial tissues but also in the extracellular spaces and stroma. As a result, the invention has overcome the barrier in using delta-catenin as a specific, non-invasive diagnostic tool for prostate and other types of cancer.

Thus the present invention provides a method for detecting or screening for the presence of cancer in a subject. In general, the method comprises obtaining, providing or collecting a tissue or fluid sample (such as a urine sample) from said subject, and then determining the presence or absence of delta-catenin in said sample, or increased levels of delta-catenin in said sample as compared to a normal or control subject. The presence of delta-catenin in said sample, or increased levels of delta-catenin in said sample, indicating said subject is afflicted with or at least at risk of developing cancer.

A further aspect of the present invention is a method as described above, wherein the presence of at least one additional cancer biomarker such as a cadherin, prostate specific antigen, and/or p120 in the subject is also detected. The presence of at least one additional biomarker indicates the subject is more likely afflicted with cancer; the absence of at least one additional biomarker indicates the subject is less likely afflicted with cancer. The use of multiple biomarkers, at least one of which is delta-cadherin as described herein, serves to reduce the number of false positives and false negatives detected by any one biomarker alone, particularly where the other biomarker is a cadherin such as E-cadherin or p120.

A further aspect of the present invention is the use of an anti-delta-catenin antibody for carrying out a method as described above.

Another aspect of the present invention is the use of a nucleic acid amplification technique such as the polymerase chain reaction (PCR), particularly reverse transcriptase-polymerase chain reaction (RT-PCR) with delta-catenin specific primers for carrying out a method as described above.

The foregoing and other objects and aspects of the present invention are explained in greater detail in the drawings herein and the specification set forth below.

BRIEF DESCRIPTION OF THE DRAWINGS

FIG. 1a. A schematic drawing illustrating the full length structure of the delta-catenin protein, consisting of 1247 amino acids. MAbD30, UB1, RAb64, RAb08, and RAb07 are epitopes to which antibodies have been made. No clear significance in protein function by these epitopes is known, but it is believed that rAb64 contains the armadillo domain that may be involved in protein-protein interaction; rAb08 contains several protein phosphorylation sites that may be important for signal transduction; rAb08 also contains a PDZ binding motif that directs binding to PDZ proteins. PDZ proteins are a diverse group of scaffolding proteins that are important to bring proteins together for function.

FIG. 1b. Expression of delta-catenin in prostate cancer (CaP). 40 ug of proteins were loaded in each lane. Lane 1 is the D30 epitope, lane 2 is the UBI epitope, etc.).

FIG. 2A and FIG. 2B. Each lane was loaded with 40 μg protein from four different types of tissue culture cells. Lane 1, cortical neurons; Lane 2, PZ-HPV-7 non-cancerous human prostate cells; Lane 3, HS-5 human bone marrow stromal cells; Lane 4, CWR-R1 human prostate tumor cells. FIG. 2A was immunoblotted with anti-delta catenin antibodies. FIG. 2B was immunoblotted with anti-actin antibodies.

FIG. 2C and FIG. 2D. Each lane was loaded with 80 μg of protein from either CWR22 xenograft tumors (Lanes 1-3) or mouse brain tissue (Lane 4). Lane 1, tissue taken at initial tumor formation; Lane 2, 2 days post-castration; Lane 3, 150 days post-castration; Lane 4, mouse brain tissue. Molecular weight is indicated on the left. FIG. 2C was immunoblotted with anti-delta catenin antibodies and FIG. 2D was immunoblotted with anti-actin antibodies. (Note that castration will reduce androgen level in the body and cause the tumor to shrink; delta-catenin expression is down 2 days after castration, which coincided with tumor shrinkage and cell apoptosis/cell death, but was back up after 150 days post-castration, a condition called tumor recurrence that is androgen independent).

FIG. 4a. Fluorescent light microscope photographs of prostate tumor cells, Panels A and B: prostate tumor cells that have well differentiated morphology show strong staining for p120ctn (A), but not delta-catenin; Panels C and D: prostate tumor cells that show more motile phenotype display strong delta-catenin staining, but a reduced p120ctn staining; Insert: higher magnification showing high expression of delta-catenin as clusters in D.

FIG. 4b. A graphic presentation of the percent cell of invasion promoted by delta-catenin as compared to a control, Lamin B dsRNA, delta-catenin dsRNA, delta-catenin cDNA. A BD Bioscience MATRIGEL™ Invasion Chamber assay was used. The chamber assay apparatus consists of two chambers. The upper chamber has a cursion of matrix protein called Matrigel and has cells plated on top of that. Invasive cells will be able to penetrate the gel and migrate to the lower chamber. More cells on the lower side of the chamber indicates higher potential for invasion.

FIG. 7A. Normal prostate tissue shows glandular structure without delta-catenin immunoreactivity.

FIG. 7B. Stage 1 tumor shows glandular structure with minimal delta-catenin immunoreactivity.

FIG. 7C. Stage 2 tumor shows enhanced delta-catenin immunoreactivity in the secretory epithelial cells of the gland without extracellular staining.

FIG. 7D. Stage 4 tumor shows strong delta-catenin immunoreactivity in the extracellular space.

FIG. 8A. Semi-quantitative immunoscore showing low immunoreactivity of δ-catenin (mean±s.e. of immunoscore=2.52±0.04) in benign samples and high immunoreactivity of δ-catenin (mean±s.e. of immunoscore=7.58±0.05) in prostatic adenocarcinomas. An immunoscore was obtained as: extent score×intensity score (range, 0 to 12).

FIG. 8B. Semi-quantitative immunoscore showing increases in mean immunoscore with prognostically increased Gleason score. The immunoscore was obtained similarly as in A.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

"Cancer" as used here includes but is not limited to brain, lung, breast, colon, prostate, esophageal, ovarian, pancreatic, adrenal, skin cancer and leukemia cells.

"Subject" as used herein refers to animal subjects, particularly mammalian subjects, including but not limited to, humans, non-human primates, dogs, cats, rabbits, goats, horses, pigs, and cattle. The subject may be a male subject or a female subject and may be of all ages including infant, juvenile, adolescent and adult subject.

"Fluid sample" or "body fluid sample" as used herein includes but is not limited to blood samples, seminal fluid, urine, and fine needle aspirates from suspected afflicted organs such as the prostate in a subject.

"Blood sample" as used here refers to whole blood, blood plasma, blood serum or any fraction thereof, so long as the fraction contains (in subject with cancer) delta-catenin as described herein.

"Antibody" as used herein refers to intact immunoglobulin molecules having binding affinity to delta-catenin, as well as immunologically active fragments thereof, such as Fab, Fab', F(ab')2, etc. Antibodies include any type of immunoglobulin and may be monoclonal, polyclonal or chimeric and may be of any species of origin, including (for example) mouse, rat, rabbit, horse, or human. See, e.g., M. Walker et al. *Molec. Immunol.* 26, 403-11 (1989), may be substituted or unsubstituted, and may be naturally occurring or synthetic.

The disclosures of all US patent references cited herein are to be incorporated by reference herein in their entirety.

The present invention is, as noted above, drawn to methods for detection of cancer utilizing delta-catenin. Detection may be for diagnostic or prognostic purposes, may be for general screening purposes, may be for targeting cancer in chemotherapy, or may be for the purpose of determining if a subject is at risk of developing cancer, confirm a diagnosis, indicate the reoccurence of cancer, etc.

One aspect of the invention is drawn to obtaining a fluid sample from a subject and determining the presence or absence of delta-catenin in said fluid sample; the presence of delta-catenin indicating that said subject is afflicted with or at least at risk for developing cancer. In one preferred embodiment, the fluid sample is a blood sample.

As noted above, the subject may be a human subject, or an animal subject for veterinary or drug screening or development purposes, with examples of suitable animal subjects including but not limited to dogs, cats, rabbits, goats, horses, pigs, cattle, etc. The subjects may be a male subject or a female subject; the subject may be of any age including including infant, juvenile, adolescent and adult subjects.

The present invention may be used to detect any type of cancer, including but not limited to esophageal, lung, breast, colon, ovarian, pancreatic, adrenal, skin cancer or leukemia. In one preferred embodiment of the invention, the cancer to be detected is prostate cancer.

As noted above, the present invention provides a method of screening for the presence of cancer in a subject, comprising the steps of: (a) contacting a biological sample taken from said subject with an antibody or delta-catenin specific primers as described above under conditions permitting said antibody or primers to specifically bind an antigen or delta-catenin nucleic acid sequences in the sample to form an antibody-antigen complex or PCR reaction complex; and then (b) determining the amount of antibody-antigen complex or delta-catenin RNA in the sample as a measure of the amount of antigen or RNA in the sample, wherein an elevated level of the antigen or RNA in the sample is associated with the presence of cancer in said subject. Other techniques for determining the quantity of delta-catenin in a subject or sample taken from a subject that do not involve antibodies and immunoassays or RT-PCR can also be used (e.g., chromatography techniques), but antibody and RT-PCR assay techniques are currently preferred.

The delta-catenin (also called "ALARM") protein and antibodies thereto are known. See, e.g., U.S. Pat. No. 6,258,929 to Kosik et al; Q. Lu et al., *J. Neurosci Res.* 67, 618 (2002), and antibodies for carrying out the present invention can be produced in accordance with known techniques. For example, monoclonal antibodies of the present invention may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120). Briefly, the procedure is as follows: an animal is immunized with antigen or immunogenic fragments or conjugates thereof. For example, haptenic oligopeptides of antigen can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody. Polyclonal antibodies used to carry out the present invention may be produced by immunizing a suitable animal (e.g., rabbit, goat, etc.) with the delta-catenin antigen, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

The step of determining the delta-catenin content of the fluid sample (for example, urine) may comprise contacting the urine sample with anti-delta catenin antibodies and measuring the amount of the anti-delta catenin-antigen complex, wherein elevated levels of antigen-antibody complex indicates the presence of cancer. Any suitable assay format can be used, a variety of which will be known to persons skilled in the art.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies as described herein may be coupled or conjugated to a solid support suitable for a diagnostic assay (e.g., beads, plates, slides or wells formed from materials such as latex or polystyrene) in accordance with known techniques, such as precipitation. Antibodies as described herein may likewise be conjugated to detectable groups such as radiolabels (e.g., $^{35}S$, $^{125}I$, $^{131}I$), enzyme labels (e.g., horseradish peroxidase, alkaline phosphatase), fluorescent labels (e.g., fluorescein), chemiluminescent labels (e.g., acridinium groups, metalloporphyrins such as phthalocyanine dyes, luminol, etc.), metal atoms (e.g., technetium-99m), etc., in accordance with known techniques. See, e.g., U.S. Pat. No. 4,472,509 to Gansow (metal chelates to monoclonal antibodies); U.S. Pat. No. 5,061,641 to Schochat et al.; and U.S. Pat. No. 4,861,869 to Nicoleotti et al. (radiolabelling proteins).

Amplification of nucleic acids may be carried out by any suitable technique, including but not limited to polymerase chain reaction (including, for RNA amplification, reverse-transcriptase polymerase chain reaction), ligase chain reaction, strand displacement amplification, transcription-based amplification (see D. Kwoh et al., Proc. Natl. Acad. Sci. USA 86, 1173-1177 (1989)), self-sustained sequence replication (or "3SR") (see J. Guatelli et al., Proc. Natl. Acad. Sci. USA 87, 1874-1878 (1990)), the Q.beta. replicase system (see P. Lizardi et al., Biotechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). The bases incorporated into the amplification product may be natural or modified bases (modified before or after amplification), and the bases may be selected to optimize subsequent electrochemical detection steps. Techniques for amplification are known and described in, among other things, U.S. Pat. Nos. 4,683,195; 4,683,202; 4,800,159; and 4,965,188; G. Walker et al., Proc. Natl. Acad. Sci. USA 89, 392-396 (1992); G. Walker et al., Nucleic Acids Res. 20, 1691-1696 (1992); R. Weiss, Science 254, 1292 (1991).

Immunoassays, or other types of assays to detect and/or quantitate the level of delta-catenin in samples as described below, may be used in screening assays to detect pathologic states associated with aberrant levels of delta-catenin expression (e.g., tumors, inflammatory states), diagnostic studies, prognostic studies, or to monitor the progression or diminution of delta-catenin expression in correlation with disease state.

Samples that may be collected for use in carrying out the immunoassay or nucleic acid assay may be blood samples or tissue samples from the organ or tissue of interest within the subject, such tissue generally of most interest being those types of tissues/cells that express differing amounts of delta-catenin in pathologic states as compared to non-pathologic states, or biological fluids such as blood (including blood fractions such as blood plasma or blood serum), urine, cerebrospinal fluid, etc). Examples may include overexpression or aberrant expression of delta-catenin in various types of malignancies as described herein, A biological sample may be a cell sample, with an intervening culturing step being performed between the time the cell sample is collected from the subject and the immunoassay is carried out on the biological sample.

A biological sample may also be a cell, cell debris, or stroma sample, with an intervening step being performed before the sample is collected from the subject to enhance the sensitivities of immunoassay.

For immunohistological techniques, a tissue sample is collected from the subject, and the presence or absence of binding of an antibody of the invention is detected. The presence of binding of the antibody in an abnormal pattern or a pattern indicative of a tumor or cancer indicates the presence of a tumor or cancer in the subject from which the tissue sample is collected. The presence of the antigen in a metastatic tumor deposit can also be used to determine a likely source of the primary tumor. Any suitable immunohistology format may be used. The tissue sample may include patient biopsies, resections or cells for cytologic study. A similar technique to immohistogy is the use of similar techniques to detect and/or phenotype cells in body fluids or other suspensions as is used for flow cytometric examination.

For in vivo diagnostic purposes the antibody according to the invention is coupled to or provided with a suitable externally detectable label, such as e.g. a radiolabel as described above or a metal atom (e.g., technetium-99m), and administered to a subject (e.g., by intravenous or intraarterial injection), in an amount sufficient to produce an externally detectable signal, whereupon the possible localized accumulation of antibody in the body is determined, with a localized accumulation of the antibody (in a region other than that which would ordinarily be expected for normal subjects or subjects free of disease) indicating the present of a tumor in that subject.

Anti-delta-catenin antibodies can be packaged in any suitable form along with instructions for carrying out the methods described herein and provided as a kit for carrying out the methods described herein, in accordance with known techniques.

Another aspect of the invention involves the use of a combination of biomarkers to reduce the frequency of false positives or false negatives by the use of any one biomarker alone. For example, where a subject is tested for δ-catenin in the manner described herein, that subject may also be tested for the presence of another biomarker. For example, the presence of at least two biomarkers indicates that the subject is more likely to be afflicted with cancer than if only one biomarker is found in that subject; the absence of at least two biomarkers indicates the subject is more likely to be free of cancer than if only one biomarker is found in that subject; the presence of one biomarker in a subject indicates the subject is more likely to be afflicted with cancer than if the subject is found to be free of another, different, biomarker, etc. Particular biomarkers that may be used in combination with the methods of testing for δ-catenin as described herein include tight junction and adherens junction proteins such as claudin and cadherin (particularly E-cadherin), prostate specific antigen, and p120 (particularly p120c$^{ctn}$).

The presence or absence of other cancer biomarkers may be detected in accordance with known techniques. Methods of detecting, diagnosing or screening for cancer (particularly prostate cancer) by detecting the presence of prostate specific antigen (PSA) are known and described in, among other things, U.S. Pat. Nos. 5,614,372; 5,840,501; 6,300,088; 6,361,955; 6,383,759; 6,423,503; and 6,482,599. Methods of detecting, diagnosing or screening for cancer (including prostate cancer) by detecting cadherins such as E-, OB-, N- and T-cadherin (particularly E-cadherin) are known and described in, among other things, U.S. Pat. Nos. 5,597,725; 5,811,518; 5,997,866; 6,682,901; and 6,723,320. Methods of detecting, diagnosing or screening for cancer by detecting p120 (including p120$^{ctn}$) are known and described in, among other things, U.S. Pat. No. 4,902,615. The disclosures of all patent references cited herein are to be incorporated by reference herein in their entirety.

The present invention is illustrated in greater detail in the following non-limiting Examples.

Experimental

Antibodies specific for delta-catenin were developed using standard techniques known in the art.

Figure 1:
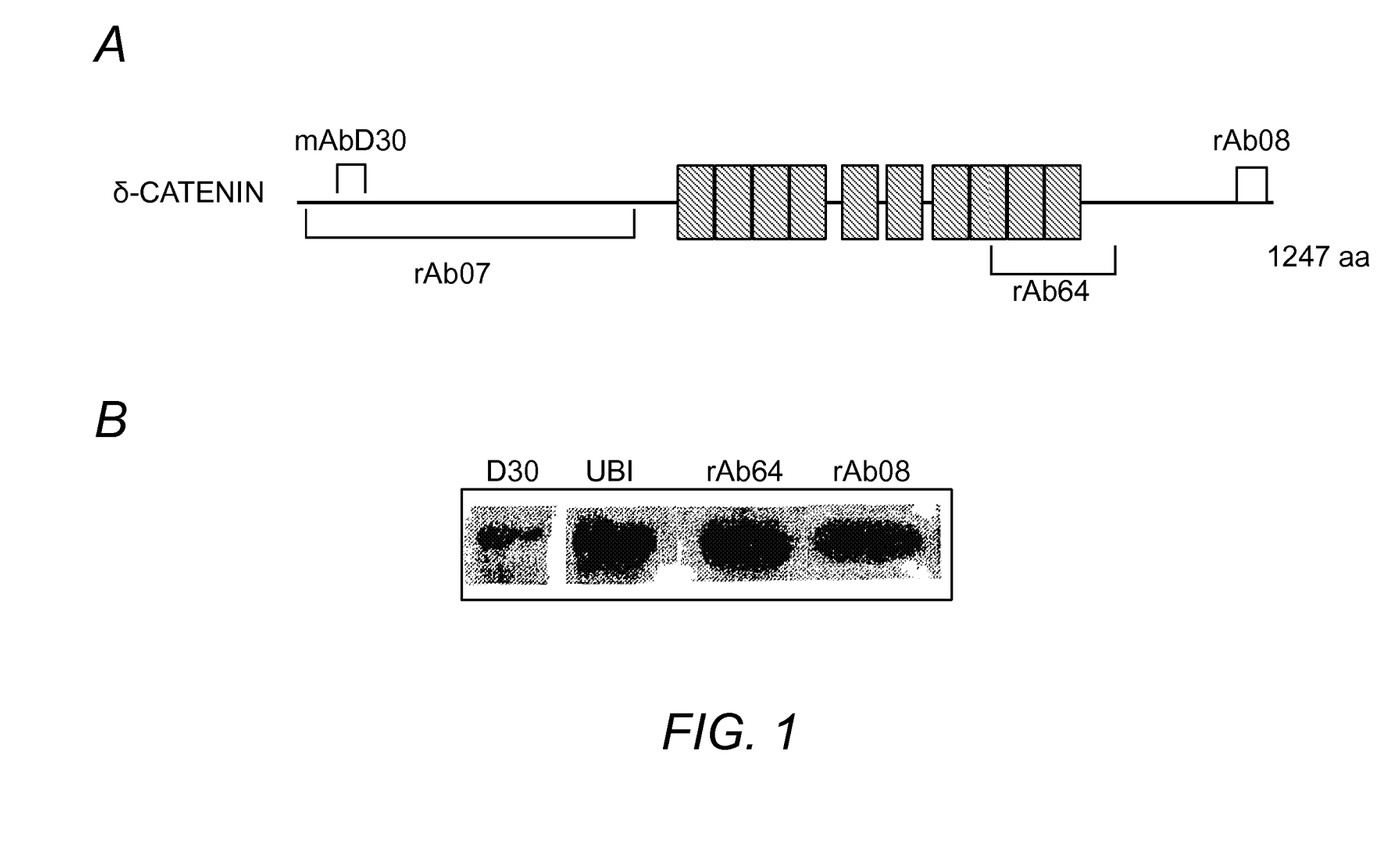
FIG. 1. Expression of delta-catenin protein in cancer and its association with cancer progression.
Figure 2:
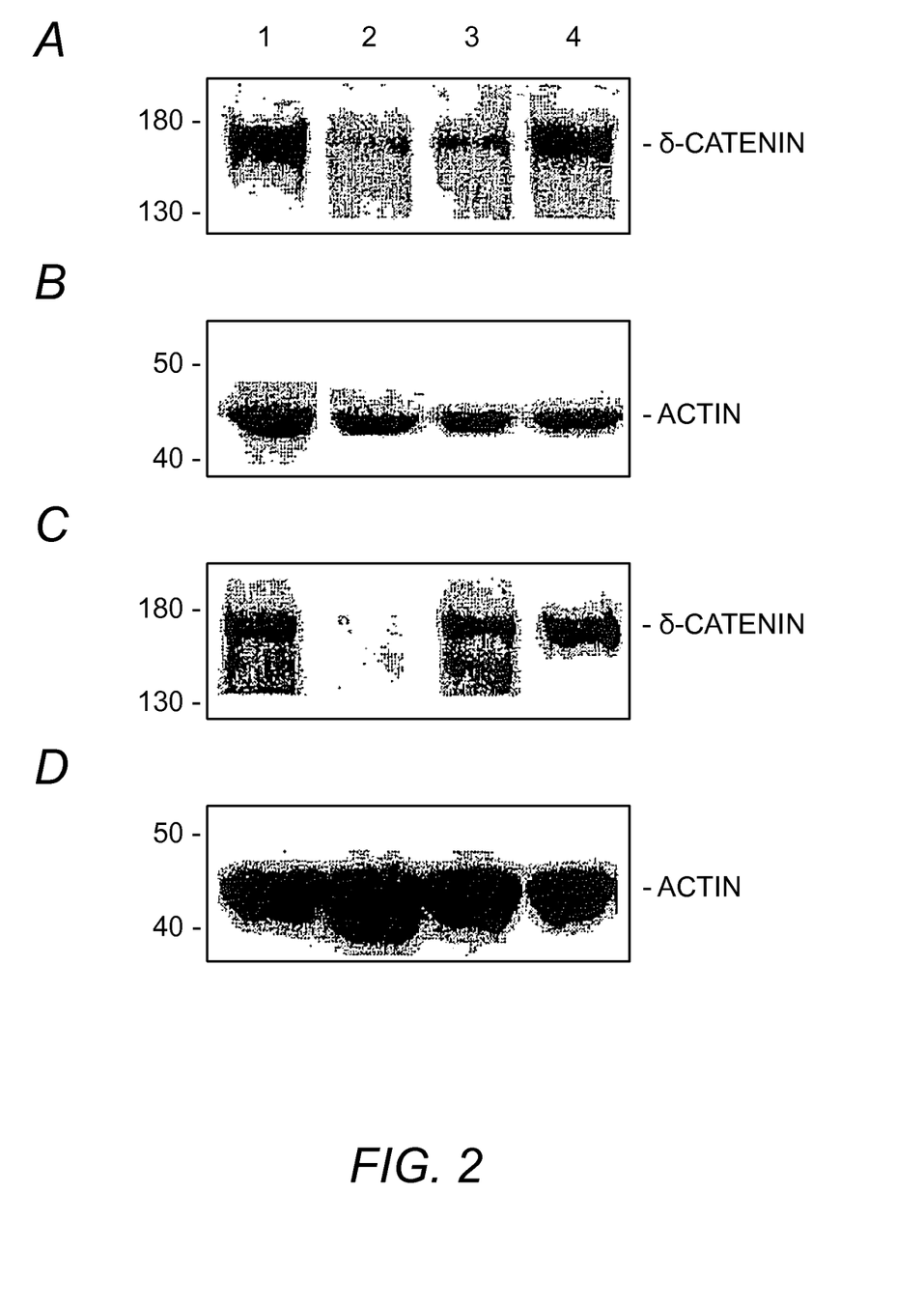
FIG. 2. Western blot demonstrating differential expression of delta-catenin in various tissues as compared to an actin control.

FIG. 1a identifies the specific epitopes of the delta-catenin protein to which the antibodies were made. Expression of delta-catenin in prostate cancer cells is shown in FIG. 1b with the each of antibodies reacting with the prostate cancer cells. FIG. 2A further demonstrates the differential expression of delta-catenin where the antibodies are shown to react specifically with cancerous prostate cells (lane 4) and not with non-cancerous prostate cells (lane 2) or bone marrow stromal cells. Additionally, as was previously known, the delta-catenin is expressed in brain tissues (FIG. 2A, lane 1 and FIG. 2C, lane 4). FIGS. 2B and 2D serve as positive controls of constitutive levels of expression and also as a control to demonstrate a constant level of protein loading. The expression of delta-catenin in the cancerous but not in the non-cancerous prostate cells demonstrates the potential improvement of this protein as a method of detecting prostate cancer over the commonly used, less sensitive PSA test.

Figure 6:
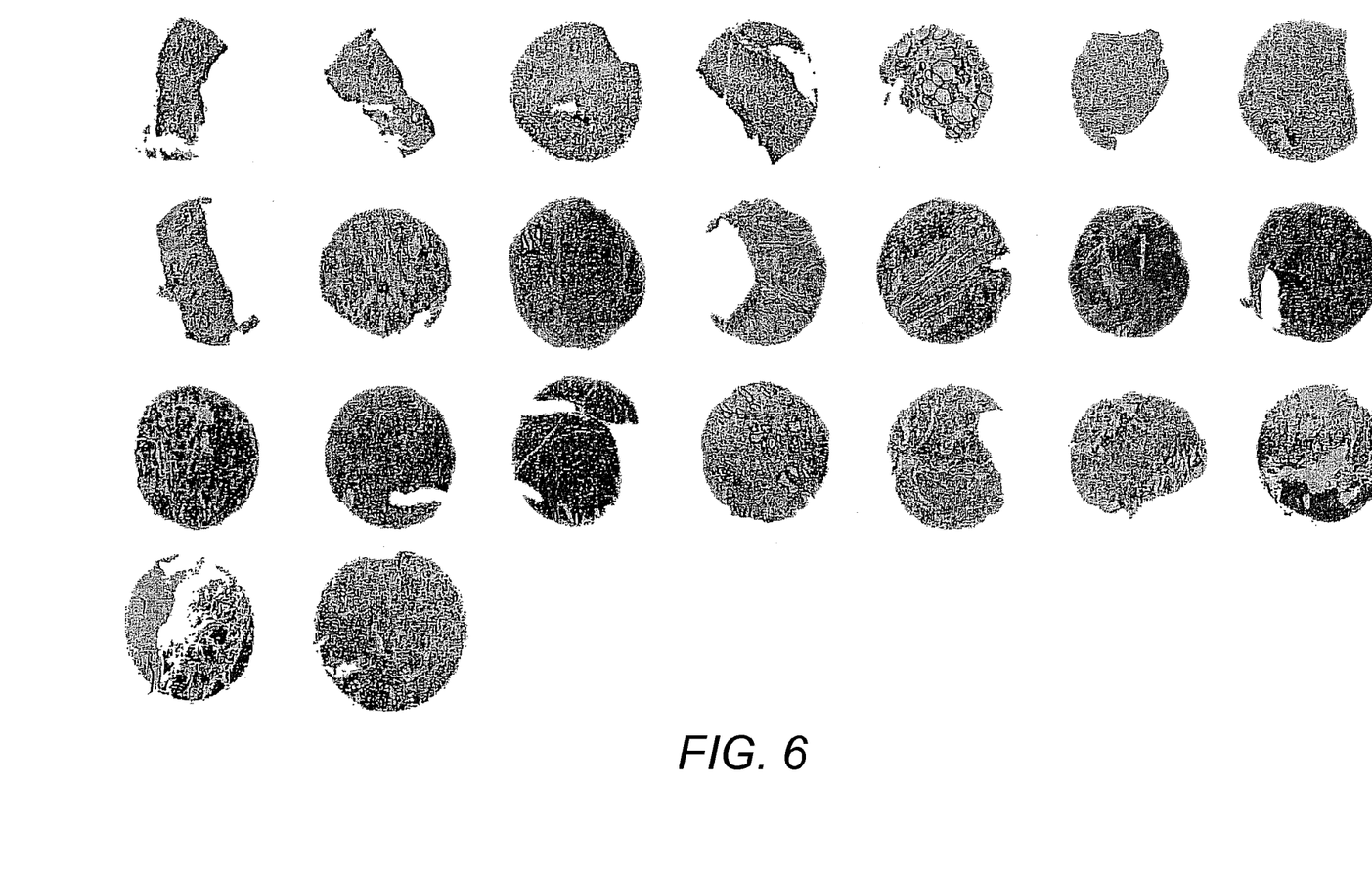
FIG. 6. Tissue Microarray showing a high percentage of prostate cancer cases with upregulated delta-catenin expression. The samples come from commercial source of prostate cancer tissues, are well characterized prostate cancer samples (meaning that the tumor grade and Gleason scores are known, and are immunostained with anti-delta-catenin).

FIG. 6 shows upregulation of delta-catenin in a high percentage of prostate cancer cases. The tissue array has many prostate cancer needle biopsy samples spotted onto slides and immunostained with anti-delta-catenin. Among these prostate cancer samples each case was identified with certain tumor grade and Gleason score to indicate the tumor stage from early, more differentiated tumore tissues to late, poorly differentiated tumor tissue that may also be very invasive. Delta-catenin overexpression was seen in many of these samples and the higher the tumor grade it is, the stronger the staining.

Figure 5:
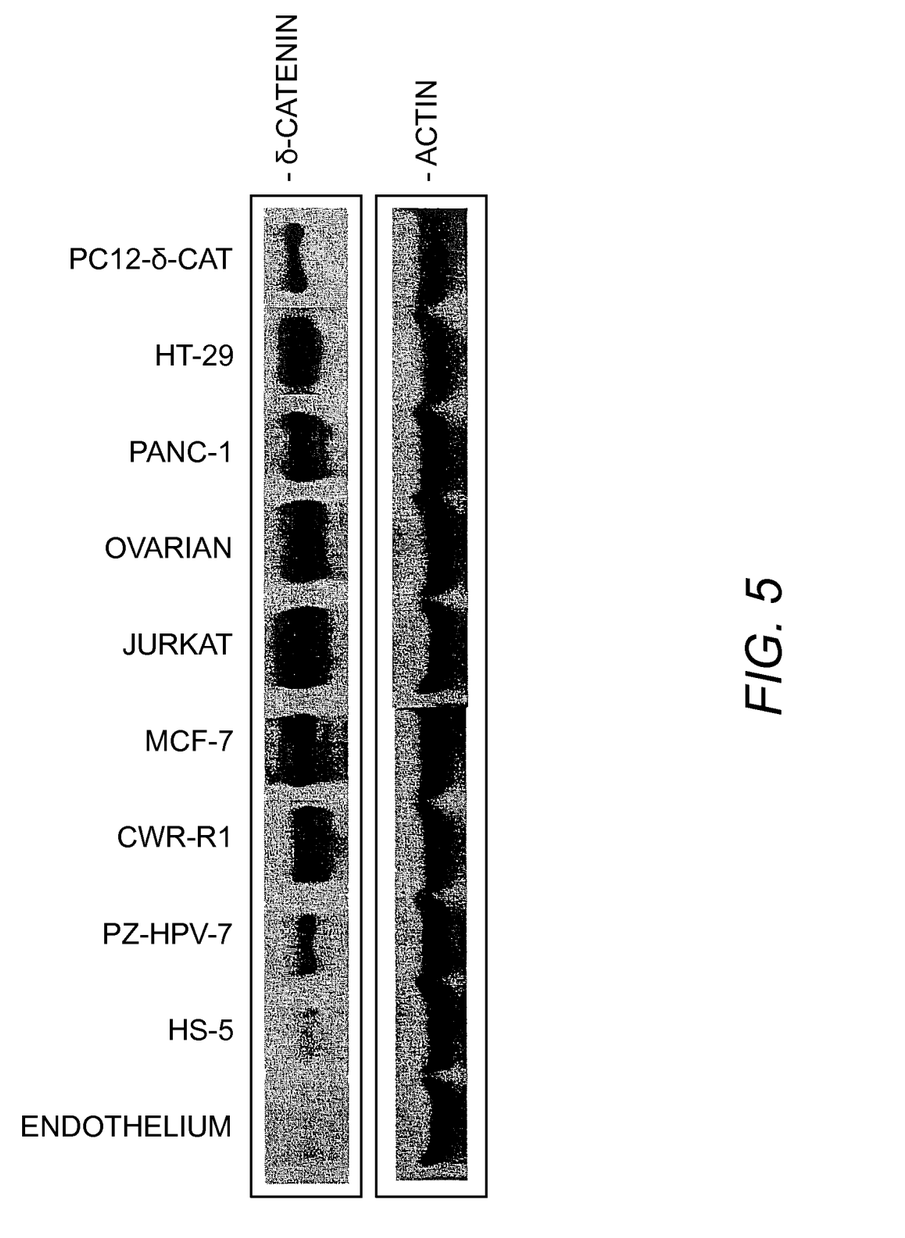
FIG. 5. Delta-catenin expression in prostate, breast, ovarian, pancreatic, colon, adrenal cancer and leukemia cells. Different cancer types were probed with delta-catenin antibody or an actin antibody control. Lane 1, endothelial cells; Lane 2, HS-5, human bone marrow stromal cell line; Lane 3 PZ-HPV-7, normal human prostate epithelial cells; Lane 4, CWR-R1, prostate cancer cell line; Lane 5, MCF-7, breast cancer cells, Lane 6, Jurkat, human leukemia T cell line, Lane 7, Ovarian cancer cells; Lane 8, Panc-1, human pancreatic cancer cell line; Lane 9, HT-29, human colon adenocarcinoma cells; Lane 10, PC12-δ-cat, pheochromocytoma cells (adrenal cancer) (δ-cat=transformed with delta-catenin). This particular figure shows the transformed PC12 cells, in which delta-catenin band is used as positive control for delta-catenin).

This invention further demonstrates the expression of delta-cateinin in a wide variety of cancer types in addition to prostate cancer (FIG. 5). Lanes 4-10 of FIG. 5A show delta-catenin expression in prostate, breast, ovarian, pancreatic, colon, adrenal cancer and leukemia cells. Delta-catenin antibody did not react with endothelial cells or bone marrow stromal cells demonstrating its differential expression in only specific tissue types (Lanes 1 and 2). FIG. 5B is an actin-antibody control to verify a constant level of protein loading. Low levels of delta-catenin were detected in prostate non-cancerous cells. So it is the level of protein rather than its presence or absence that is of greatest importance. In general, the level of delta-catenin in normal tissue is very low, except for brain; In this case, the cell line PZ-HPV-7 is a non-cancerous cells, but to make it immortal and can grow in culture, it is trnasformed with HPV). The tissue IHC, though, shows clearly that delta-catenin staining in normal prostate tissue is extremely low.

Figure 3:
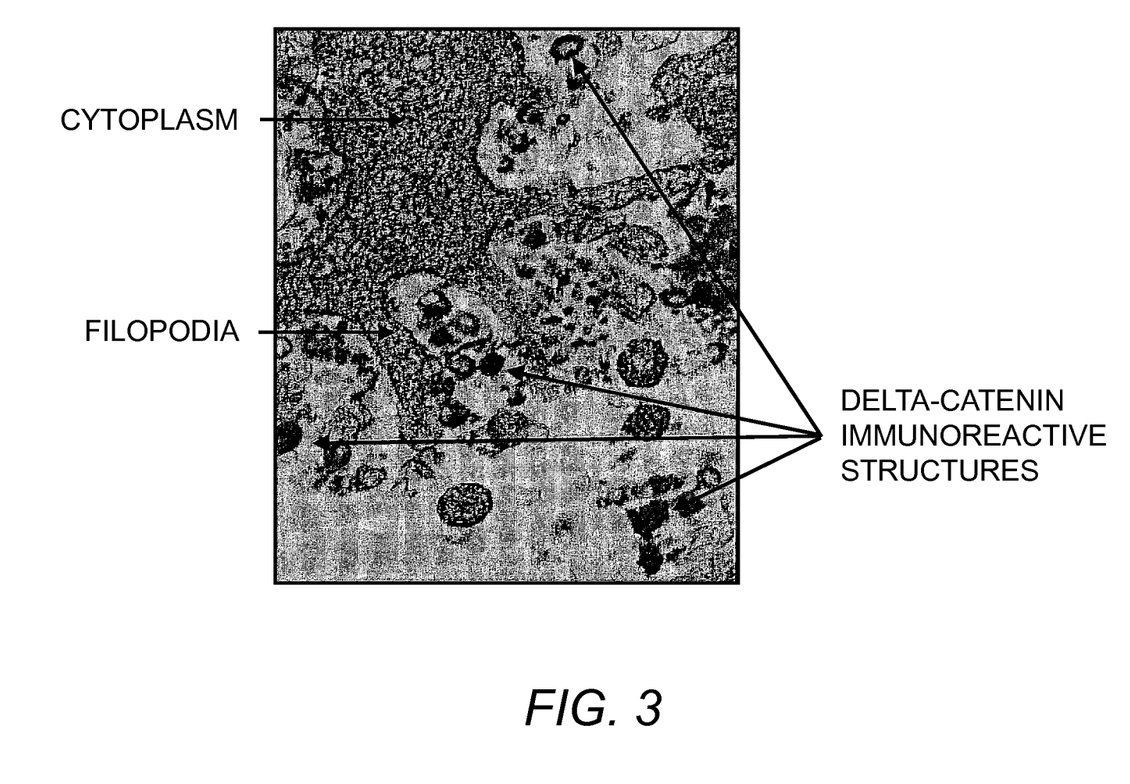
FIG. 3. A transmission electron micrograph showing excretion of delta-catenin into extracellular spaces by cells in which the protein is being over-expressed. Arrows indicate the structures reacting with delta-catenin antibody.
Figure 4:
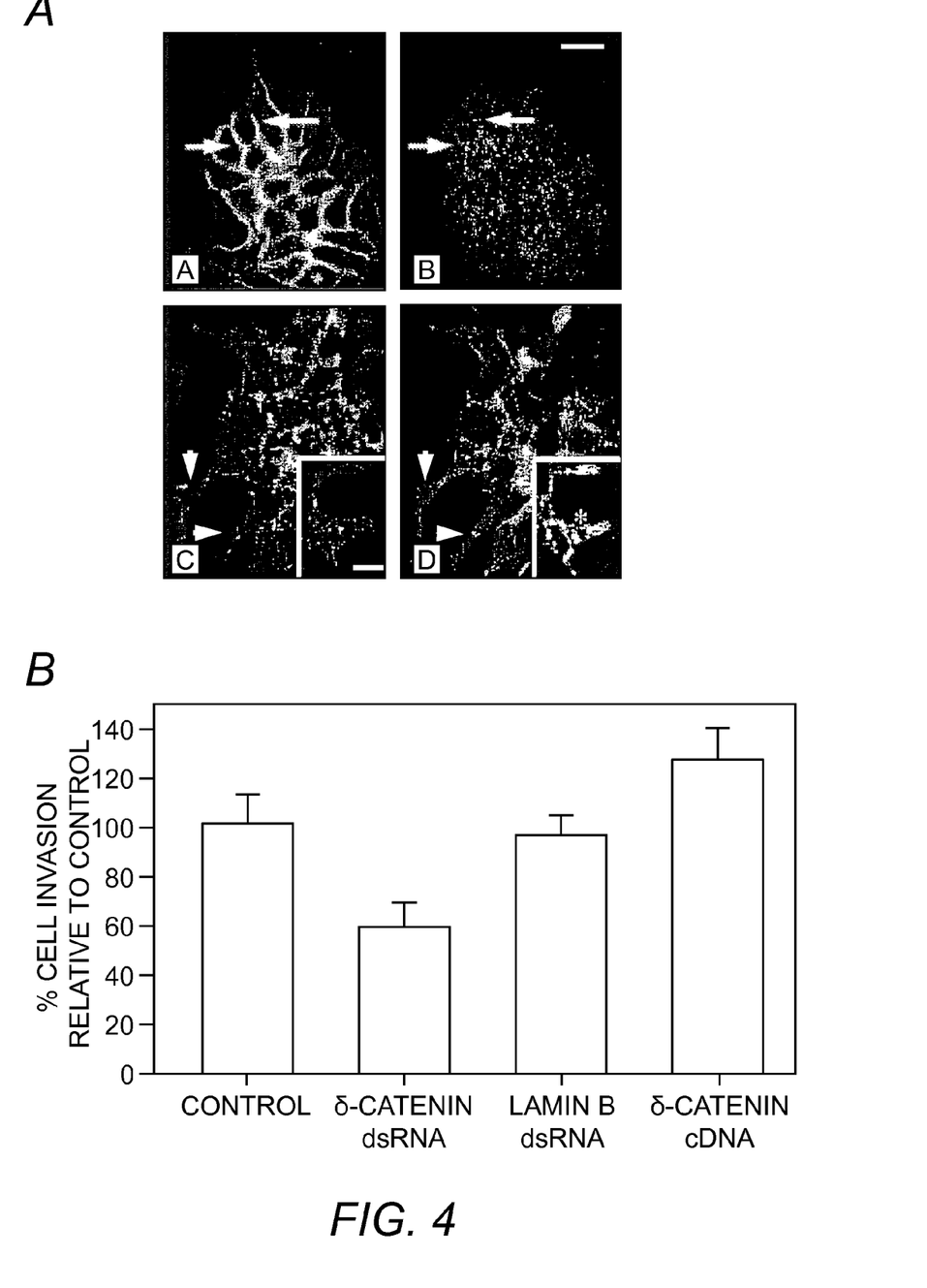
FIG. 4. Evidence of promotion of cell invasion by delta-catenin.
Figure 7:
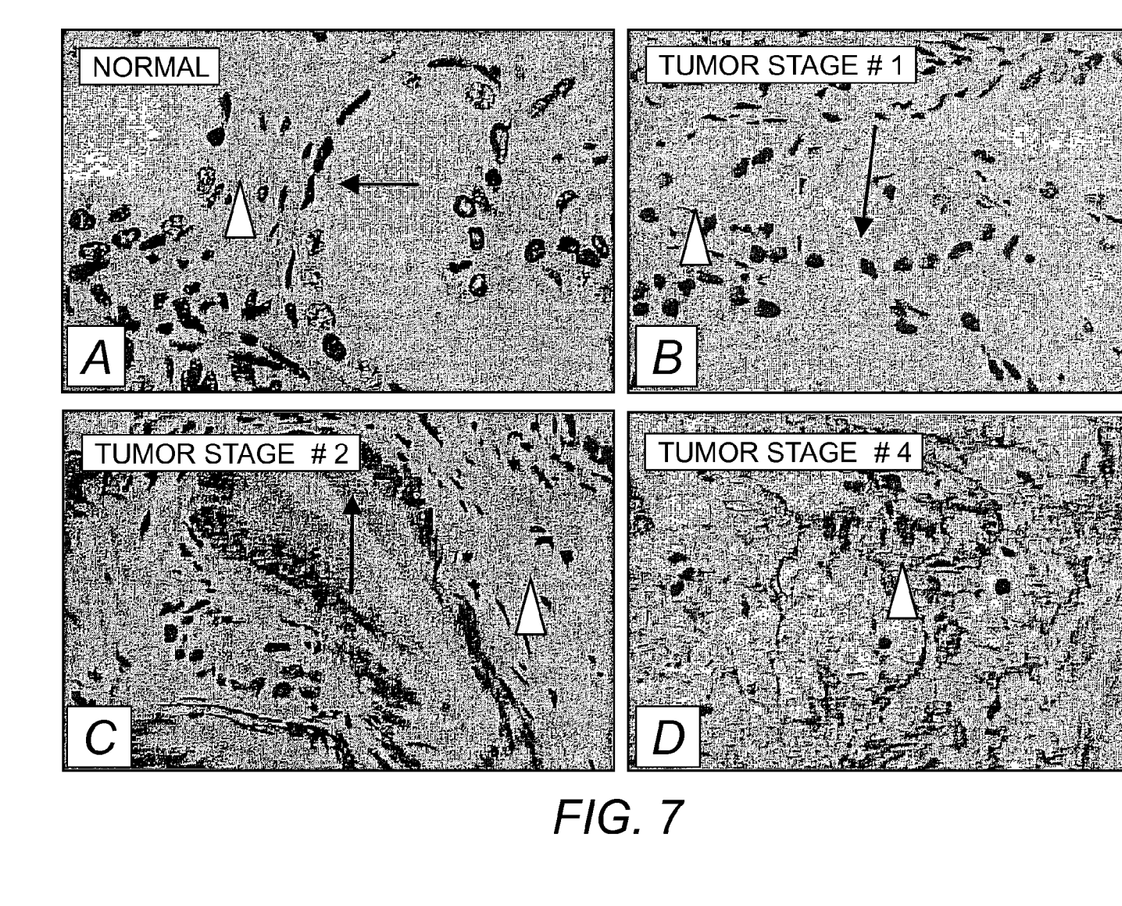
FIG. 7. Delta-catenin overexpression in the extracellular spaces of prostate cancer tissue. Arrows point to glandular secretory epithelial cells, whereas arrowheads point to extracellular matrix and stroma).

This invention for the first time demonstrates delta-catenin expression in extracellular spaces (FIGS. 3 and 7). The transmission electron micrograph (FIG. 3) of cells overexpressing delta-catenin. shows extracellular structures that are immunoreactive with delta-catenin antibody. The progression of expression of delta-catenin expression in different stage prostate tumors is shown in FIG. 7. Normal prostate glandular tissue showed no immunoreactivity with delta-catenin antibodies (FIG. 7A). Stage 1 and stage 2 prostate tumor tissues (FIGS. 7B and 7C) showed minimal to enhanced intracellular levels of delta-catenin immunoreactivity, respectively, while stage 4 tumor tissue (FIG. 7D) showed strong delta-catenin immunoreactivity in the extracellular spaces. Extracellular expression of delta-catenin is an important aspect in the development of delta-catenin as a non-invasive test for prostate cancer because it will allow the sampling of bodily fluids and not just tissues.

Experimental 2

Materials.

Mouse anti-E-cadherin, mouse anti-pp120 and mouse anti-δ-catenin D30 (to amino acids 85-194) were from BD Biosciences (Palo Alto, Calif.). Affinity purified rabbit anti-human δ-catenin was developed as previously described (Lu, Q., et al., *J Cell Biol.* 144 (3): 519-532, 1999; Ho, C. et al., *J Comp Neurol,* 420 (2): 261-276, 2000). They were raised against amino acids 434-530 (rAB62), amino acids 828-1022 (rAb64), and amino acids 1213-1225 (rAb25). Mouse anti-actin was from Oncogene science (Boston, Mass.). Unless otherwise indicated, all chemicals were from Sigma (St. Louis, Mo.).

Cell Culture and cDNA Transfection.

PC12 cells were grown in DMEM with 10% heat inactivated horse serum and 5% fetal bovine serum (FBS). Human endothelial cell lysates were obtained from BD Biosciences (Palo Alto, Calif.). Non-tumorigenic prostate epithelial PZ-HPV-7 (ATCC, Rockville, Md.) was cultured in serum-free karotinocyte medium, while tumorigenic prostate cancer CWR-R1 was cultured in Richter's improved minimal essential medium (Invitrogen, Carlsbad, Calif.) supplemented with epidermal growth factor (EGF), insulin/transferin/selenium, nicotinamide, linoleic acid, and FBS, as described by Wu and Terrian (*J Biol Chem.* 277(43): 40449-40455, 2002). Primary hippocampal cultures were prepared as described by Goslin and Banker (1998) with minor modifications (Lu, Q. et al., *J Cell Biol.* 144 (3): 519-532, 1999; Jones, S. B. et al., *Neuroscience* 115 (4): 1009-1021, 2002). Briefly, 18-day timed pregnant rats were sacrificed, and the embryos were removed in accordance with the NIH Guide for the Care and Use of Laboratory Animals. Hippocampi and cortices were collected, and cells were dissociated by trypsinization and plated onto poly-L-lysine coated coverslips and cell culture plates, respectively. After neurons adhered to the substrate, the medium was changed over to B-27 supplemented Neurobasal. All cultures were maintained at 37° C. with 5% $CO_2$ until they were either fixed or lysed for immunochemical analysis.

Some cells were transfected with δ-catenin cDNA to evaluate the effects of δ-catenin overexpression on $p120^{ctn}$ expression and distribution. For neuronal cultures, hippocampal neurons grown for 5 days in vitro (DIV) were transfected with pEGFP (Clontech, Palo Alto, Calif.) as control, or with pEGFP-δ-catenin using Lipofectamine 2000 reagent (Life Technologies Grand Island, N.Y.) according to instructions provided. Transfection of PZ-HPV-7 and CWR-R1 cells were performed with using Lipofectinamine-Plus method.

Protein Extraction and Immunoblotting.

Cultured cells were lysed in a radioimmunoprecipitation assay (RIPA) buffer containing 10 mM HEPES, pH 7.3, 150 mM NaCl, 2 mM EDTA, 1% Triton X-100, 0.5% deoxycholate, 0.2% SDS with protease inhibitor cocktails. Insoluble materials were removed by centrifugation. For human benign and prostate tumor tissues, cell lysates were prepared from the frozen peripheral zones of prostatic acinar tissues by extraction in 150 mM NaCl, 50 mM Tris, pH 7.5, with 0.5% NP-40% with 1 mM sodium vanadate, 1 mM Na Fluoride, 1 mM PMSF, 10 ug/ml leupeptin, 10 ug/ml pepstatin, and 10 ug/ml aprotinin. The lysates were mixed with sample buffer and equal protein amounts were loaded for SDS-PAGE analysis. After proteins were transferred to nitrocellulose membranes (PGC Scientifics, Frederick, Md.), anti-δ-catenin (1:500 for rabbit antibodies and 1:300 for mouse antibodies) and anti-actin (1:5000) immunoreactivities were revealed by antibody immunoblotting using enhanced chemiluminescence (Amersham Life Science, Piscataway, N.J.) for detection. When necessary, blots were stripped with 100 mM β-mercaptoethanol, 2% SDS, and 62.5 mM Tris-HCl, pH 7.6 for 30 minutes at 55° C. The blots were then washed in Tris buffer containing 0.1% Tween 20 before re-probing with different antibodies.

RNA isolation and RT-PCR.

The total RNA was isolated by guanidinium thiocyanate-phenol-chloroform extraction (Jeansonne, B. et al., *Cell Mol Biol.* 49 (1): 13-21, 2003). To synthesize the first-strand DNA sequence from the total RNA, random decamers were used as a first-strand primer (Ambion Inc, Austin, Tex.). The specific PCR primers chosen to yield the 283 bp fragment of δ-catenin are as follows: forward (5'-3'), TACTCCGCAAGACGACT-GACC (SEQ ID NO: 1), and reverse (5'-3'), CCATCA-CACTCTCTCATCCTTCTG (SEQ ID NO: 2). The annealing temperature in the PCR reaction is 56° C. Some of the RT-PCR products were purified from the DNA gel and verified by the DNA sequencing to confirm the δ-catenin sequence.

Tissue MicroArray Specimens.

The Tissue MicroArray (TMA) block was constructed from archival paraffin blocks of radical prostatectomy (RP) cases performed at Vanderbilt University Medical Center from January 1998 to December 2001, RP specimens were submitted in their entirety for whole mount processing. Total tumor volume by digital planimetry, Gleason score, tumor stage, and status of surgical margins were assessed as described (Brooks, J. D. Microarray analysis in prostate cancer research. Curr Opin Urol. 12 (5): 395-399, 2002). Ninety cases were retrieved from a maintained RP Pathology database to achieve the following grade and stage combinations: 15 Gleason score 5 or 6, pT2; 15 Gleason score 5 or 6, pT3; 15 Gleason score 7, pT2; 15 Gleason score 7, pT3; 15 Gleason score≥8, pT2; 15 Gleason score≥8, pT3 (Chung, C. H. et al., Nat Genet. 32 Suppl: 533-540 (2002); Feroze-Merzoug, F. et al., Cancer Metastasis Rev. 20 (3-4): 165-171 (2001)). Portions of tumor representative of the case were identified by review of tumor maps and individual whole mount slides. Representative areas of tumor and benign (typically peripheral zone), corresponding to the zone of origin of the prostate cancer in the vast majority of cases (Brooks, supra), were identified on whole mount slides and matched to the corresponding paraffin blocks. The TMA block was constructed with a Beecher Instruments Tissue Array (Silver Spring, Md.) utilizing two representative 0.6 mm areas of tumor and one 0.6 mm area of benign per case (total of 270 samples).

Immunohistochemistry.

For immunohistochemistry, 5 μm sections were cut from the TMA block onto charged glass slides. The TMA slides were subjected to antigen retrieval for all antibodies. After deparaffination and rehydration, tissue sections were placed in a pressure cooker on high for 15 minutes in Trilogy retrieval solution (Cell Marque, Hot Springs, Ark.). Sections were then immunostained with rabbit anti-δ-catenin, mouse anti-E-cadherin or anti-p120$^{ctn}$ using Dako Autostainer with the LSAB 2 protocol (labeled streptavidin-biotin method, Dako Corp, Carpenteria, Calif.). The streptavidin-biotin reaction was detected using diamionobenzidine as a substrate. All sections were counterstained with Hematoxilin and coversliped using a Sakura Tissue Tek (Sakura Corp, Torrance, Calif.). TMA immunostaining was assessed in benign and tumor samples in a blinded manner for both extent and intensity of immunoreactivity. Extent of immunostaining on one section was defined as the epithelial area that showed positive δ-catenin immunoreactivity and was scored semi-quantitatively as follows: 0, absent; 1+, <25%; 2+, 25-50%; 3+, 51-75%; 4+, >75%. Intensity of immunostaining was scored semi-quantitatively as follows: 0, negative; 1+, weak; 2+, moderate; 3+, strong.

Two pathologists from two different groups assigned Gleason scores for the TMA independently. When the TMA slides were studied for δ-catenin immunoreactivity, one analysis was performed with the aid of automated digital reading and an immunoscore was obtained as: extent score×intensity score (range, 0 to 12). In another analysis, manual reading was applied, and the immunoscores for the staining intensity and staining extent were assigned separately. For tumors with both samples (two representative 0.6 mm areas as described above) present, the immunoscore was the mean of the two scores for the separately assessed samples. They were analyzed semi-quantitatively by light microscopy equipped with MetaMorph imaging software (Universal Imaging Corp. West Chester, Pa.).

Data and Statistical Analyses.

To examine the relationship among δ-catenin, E-cadherin and p120$^{ctn}$, the serial sections were photographed and the distribution and expression of these proteins were analyzed. Statistical analysis was performed using MS Excel and SigmaPlot 5.0 (SPSS Science, Chicago, Ill.). Student t-tests were conducted and p-value was assigned. The significance level was set at 0.05.

Results

δ-Catenin is Overexpressed in Prostate Cancer Cells.

Previous studies indicated that δ-catenin mRNA is expressed in tumor cell lines (Lu et al., supra 1999; Lu, Q. et al., J Neurosci Res. 67 (5): 618-624, 2002), and is overexpressed in prostate cancer in comparison to benign prostate hyperplasia (BPH) (Burger, M. J. et al., Int J Cancer 100(2): 228-237, 2002). To determine if δ-catenin protein expression is increased in prostate cancer cells, we first compared human marrow stromal cells HS-5 and non-cancerous human prostate epithelial cells PZ-HPV-7 with CWR-R1, a cell line derived from a recurrent CWR22 human prostate tumor xenograft (Pretlow, T. G. et al., J Natl Cancer Inst. 85 (5): 394-398, 1993; Wainstein, M. A. et al., Cancer Res. 54 (23): 6049-6052, 1994; Nagabhushan, M. et al., Cancer Res. 56 (13): 3042-3046, 1996; Gregory, C. W. et al., Cancer Res. 61(7): 2892-2898, 20010). Although Western Blots showed that δ-catenin is expressed in all of the cell lines, its expression in CWR-R1 cells is significantly higher than in HS-5 and PZ-HPV-7 cells (data not shown). δ-Catenin immunoreactivity is authentic since it co-migrates with δ-catenin in cortical neurons (data not shown), where δ-catenin expression has been well established (Lu et al., 1999; Lu et al., 2002; Jones, S. B. et al., Neuroscience 115 (4): 1009-1021, 2002). δ-Catenin expression in CWR-R1 cells has also been confirmed by the use of four independent δ-catenin antibodies: mAbD30, which recognizes amino acids 85-194; rAb62, which recognizes amino acid residues 434-530; rAb64, raised against amino acid residues 828-1022; and rAb25, an antibody that recognizes amino acid residues 1201-1225 (data not shown). To determine if the enhanced level of δ-catenin protein in cancer cells detected by Western Blot might be due to an increased mRNA expression of δ-catenin gene, we applied RT-PCR and found that CWR-R1 cells displayed increased amounts of δ-catenin mRNA when compared with PZ-HPV-7 cells (data not shown). These results demonstrated that δ-catenin protein is overexpressed in prostate cancer cells in vitro. In addition, an enhanced mRNA expression is at least partially responsible for the overexpression of δ-catenin.

δ-Catenin Expression is Increased in Human Prostatic Adenocarcinomas.

In the only study to previously examine changes in δ-catenin expression in cancerous tissues, Burger et al (Id) compared δ-catenin mRNA expression using real-time PCR in 16 prostate tumor and 11 BPH tissue samples. These investigators reported that levels of δ-catenin mRNA expression in all tumor samples examined were higher than in any of the BPH samples. However, no correlation between δ-catenin mRNA expression and tumor progression was observed (Id.). To extend this study of the association between δ-catenin expression and the progression of human prostate cancer, an immunohistochemical analysis of the δ-catenin protein expression in human prostatic adenocarcinomas was conducted using Tissue MicroArray (TMA).

Figure 8:
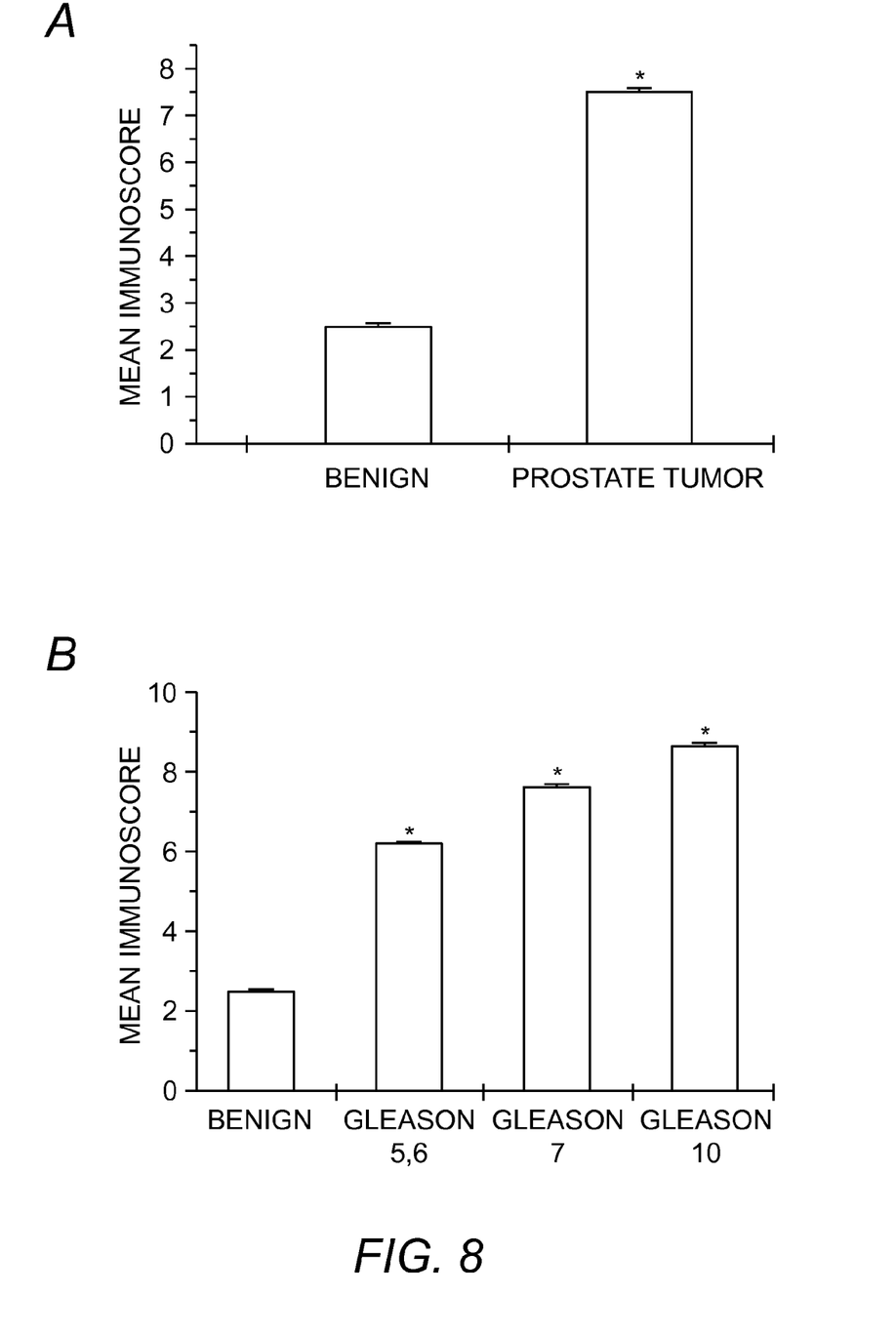
FIG. 8. δ-Catenin overexpression in primary human prostatic adenocarcinomas.

We have performed immunohistochemistry on TMA samples that contained 90 cases of prostatic adenocarcinomas and 90 benign prostatic tissue samples (data not shown). Two pathologists from two groups independently assigned Gleason scores to the tumor specimens. One pathologist determined the Gleason scores without prior knowledge of patient information. In one analysis, an immunoscore was obtained as: extent score×intensity score (range, 0 to 12, see Material and Method). An estimated 85% of the prostate cancer specimens showed enhanced immunoreactivity when compared to the benign prostatic tissue samples from the peripheral zones of the glands (Table I). The mean±s.e. of the immunoscore for benign samples was 2.52±0.04. For tumor samples, the mean±s.e. of the immunoscore was 7.58±0.05 (FIG. 8A). In 65 of 90 cases, both benign and tumors can be compared and assessed. The immunoscore was increased in tumor versus benign in 55 of 65 cases (or 85%); whereas the immunoscore of cancer and benign samples was equal in 6 out of 65 (or 9%) cases, and the immunoscore was higher in benign versus tumor in only 4 out of 65 (or 6%) cases (Table I). The mean tumor scores appeared to increase with prognostically significant increased Gleason scores. In this analysis, we observed an immunoscore of 6.24 in the tumors with Gleason score 5,6; an immunoscore of 7.69 in the tumors with Gleason score 7; an immunoscore of 8.75 in tumors with Gleason score≥8 (FIG. 8B).

In an independent experiment in which protein lysates from 8 cases of high-grade prostate tumors were compared to 8 cases of benign prostate tissues sampled from the peripheral zone of the glands, δ-catenin showed an increased immunoreactivity in 5 cases or ~63% of all specimens (data not shown). Semi-quantitative analysis showed that δ-catenin immunoreactivity in prostate cancer lysates increased approximately 80% when compared to that in benign samples.

When prostate gland images were analyzed, anti-δ-catenin immunostaining was very weak in benign tissues (data not shown). In the prostatic adenocarcinomas with low tumor grade, δ-catenin staining was localized to the secretory glandular epithelial cells (data not shown). The number of δ-catenin-positive cells expanded in prostate cancer samples with high tumor grade (data not shown).

These results together demonstrated that δ-catenin expression is increased in primary human prostatic adenocarcinomas.

Increased Expression of δ-Catenin is Associated with the Downregulation of E-Cadherin and p120$^{ctn}$ in Human Prostatic Adenocarcinomas.

In the second analysis in which consecutive sections were immunostained with anti-δ-catenin, anti-E-cadherin and anti-p120$^{ctn}$, extent score and intensity score were determined separately to see if the results might be different from that obtained in the first analysis described above. Here, 92% of the prostate cancer samples showed strong (46 out of 72 cases) or moderate (20 out of 72 cases) staining (immunoscore equal or above 2) for δ-catenin, only 6 out of 72 (or 8%) of the specimens was either negative or with immunoscore below 2 (Table II, Cancer). Interestingly, while 49 out of 65 cases (or 75%) of benign specimens showed an immunoscore of below 2, 6 out of 65 (or 9%) of benign samples showed an immunoscore equal to 2, and 10 out of 65 (or 15%) of benign specimens showed an immunoscore above 2. This data indicates that a small percentage of cases will be falsely judged positive for prostate cancer if benign specimens are evaluated using δ-catenin immunoscore as the sole criteria.

When anti-E-cadherin immunoreactivity was analyzed, 96% of benign specimens showed strong (64 out of 71 cases) or moderate (4 out of 71 cases) staining (immunoscores equal or greater than 2), only 3 out of 71 cases (or 4%) of the benign specimens showed an weak immunoreactivity (less than 2), indicating an excellent correlation between strong E-cadherin expression and benign prostate tissues (Table II). However, anti-E-cadherin immunoreactivity was strong (39 out of 89 cases) or moderate (20 out 89 cases) in 66% of the prostate cancer cases, with only 30 out of 89 cases (or 34%) showed an immunoscore lower than 2. These observations showed that relying on E-cadherin immunoreactivity alone could have very high probability of missing prostate tumors, especially in the low Gleason score tumors. It should be noted that these data were derived from the average of total prostate cancer cases. In the most aggressive cases of prostatic adenocarcinomas (Gleason score>8), over 71% (or 10 out of 14 cases) of the specimens showed a sharply reduced immunoscores below 2, consistent with the literature that E-cadherin is down regulated in the more advanced prostatic adenocarcinomas.

In benign specimens, anti-p120$^{ctn}$ showed an overwhelmingly strong immunoreactivity of above immunoscore 2 (71 out of 71 cases or 100%). However, 62 out 88 cases (or 70%) of the prostatic adenocarcinomas retained fairly strong anti-p120$^{ctn}$ immunoreactivity of above 2, with only 21% of the cases showing immunoscore below 2 (Table II). This indicates that additional biomarkers is necessary to compensate for p120$^{ctn}$ for detecting prostate cancer, particularly in the low Gleason score tumors. Similar to anti-E-cadherin immunostaining, anti-p120$^{ctn}$ staining was dramatically reduced in the more aggressive cases of prostatic adenocarcinomas (Gleason score>8), consistent with the notion that both E-cadherin and p120$^{ctn}$ are tumor suppressors.

Using δ-Catenin, E-Cadherin and p120$^{ctn}$ as Biomarker Cluster Improves the Probability of Predicting or Excluding Prostate Cancer.

We further analyzed the data set to determine whether E-cadherin and p120$^{ctn}$ immunoreactivity can be used to correct the false negative results associated with the 8% of the prostate cancer cases that showed weak anti-δ-catenin immunoreactivity. Our hypothesis was that from these 6 cases where δ-catenin immunoscore was weak, perhaps the δ-catenin epitopes were not preserved appropriately during tissue processing, or δ-catenin level in some patients was inherently low. If this was the case, employing anti-E-cadherin or anti-p120$^{ctn}$ may circumvent the problem of misdiagnosis. Indeed, in these 6 cases that showed weak δ-catenin immunoreactivity, anti-E-cadherin staining of the consecutive sections was able to correctly predict prostate cancer in 4 cases (or 67%), while anti-p120$^{ctn}$ immunoreactivity can compensate for 83% of the time (or 5 out of 6 cases) (Table III). The probability to correct these 6 false negative cases stands at 83% when both data from anti-E-cadherin and anti-p120$^{ctn}$ staining were used (Table IV). This would result in only 1 case out of total 72 prostatic adenocarcinomas (or 1.4%) that showed a false negative in predicting prostate cancer when examining δ-catenin, E-cadherin and p120$^{ctn}$ as a biomarker cluster.

As shown above, anti-E-cadherin and anti-p120$^{ctn}$ showed strong immunostaining in both benign and the majority of prostatic adenocarcinomas, particularly in the low Gleason score specimens. Therefore, although the down regulation of these two proteins was closely associated with the high Gleason score prostatic adenocarcinomas, it would not be safe to rely on these markers to predict early stage prostate cancer. Table II showed that, in 39 out of 89 (or 44%) of the prostate cancer specimens, E-cadherin immunoreactivity remained strong. When these 39 cases were evaluated for anti-δ-catenin and anti-p120$^{ctn}$ staining, 24 out of 39 cases (or 62%) showed strong immunoreactvity for δ-catenin and 5 out of 39 cases (or 13%) showed reduced immunostaining of p120$^{ctn}$ (Table III). Because the correction by δ-catenin and p120$^{ctn}$ immunoreactivity happened in the overlapping cases, there was a total 62% of chances that these prostate cancer cases will be discovered if all three biomarkers were used in predicting prostatic adenocarcinomas (Table IV). In prostate cancer specimens, 62 out of 88 (or 70%) of the specimens showed strong anti-p120$^{ctn}$ immunoreactivity, while only 18 out of 88 (or 21%) of the cases displayed a clearly reduced anti-p120$^{ctn}$ staining intensity (Table II). The majority of these 18% cases came from the high Gleason score prostatic adenocarcinomas. When anti-δ-catenin immunoreactivity in these 62 cases was analyzed, 31 cases (or 58%) showed enhanced immunoscores, whereas 29 out of 62 cases (or 47%) showed reduced E-cadherin signal, consistent with the presence of prostatic adenocarcinomas in these cases (Table III). Therefore, here the combination of anti-δ-catenin and E-cadherin immunostaining can correctly detect 49 out of 62 (or 79%) prostate cancer cases that otherwise would be judged falsely negative using anti-p120$^{ctn}$ immunostaining as the only criteria (Table IV).

Similarly, using δ-catenin, E-cadherin and p120$^{ctn}$ as biomarker cluster can reduce false positive outcomes and increase the probability in excluding prostate cancer misdiagnosis in benign populations. For example, 7 cases of benign tissues showed moderate or reduced anti-E-cadherin immunoreactvity (Table II). Anti-δ-catenin immunoreactivity was able to correct 4 out of 7 cases (or 57%). 10 cases (or 15%) of benign tissues showed strong anti-δ-catenin immunoreactivity, while 6 cases (or 9%) of benign samples showed moderate anti-δ-catenin immunoreactivity. This result suggested that 16 out of 65 benign cases might be misinterpreted as having prostate cancer. When these cases were examined using anti-E-cadherin as a marker, 13 of them (or 81%) showed strong immunoreactivity. Although all benign specimens (71/71 or 100%) showed strong anti-p120$^{ctn}$ immunoreactivity (Table II), p120$^{ctn}$ immunoreactivity is also strong in many cases of early stage prostatic adenocarcinomas. Therefore, relying on p120$^{ctn}$ immunoreactivity alone may lead to false negative results. Since most of the prostate cancer cases that showed falsely strong E-cadherin and p120$^{ctn}$ staining did not show the same falsely weak δ-catenin staining (Table III and Table IV), the non-overlapping nature of the false positive and false negative cases suggest that it is possible to exclude many of the false positive outcomes if these three biomarkers are used for analysis.

Increased δ-Catenin Expression is Associated with the Down Regulation of E-Cadherin and p120$^{ctn}$ During the Progression of Prostatic Adenocarcinomas.

Figure 9:
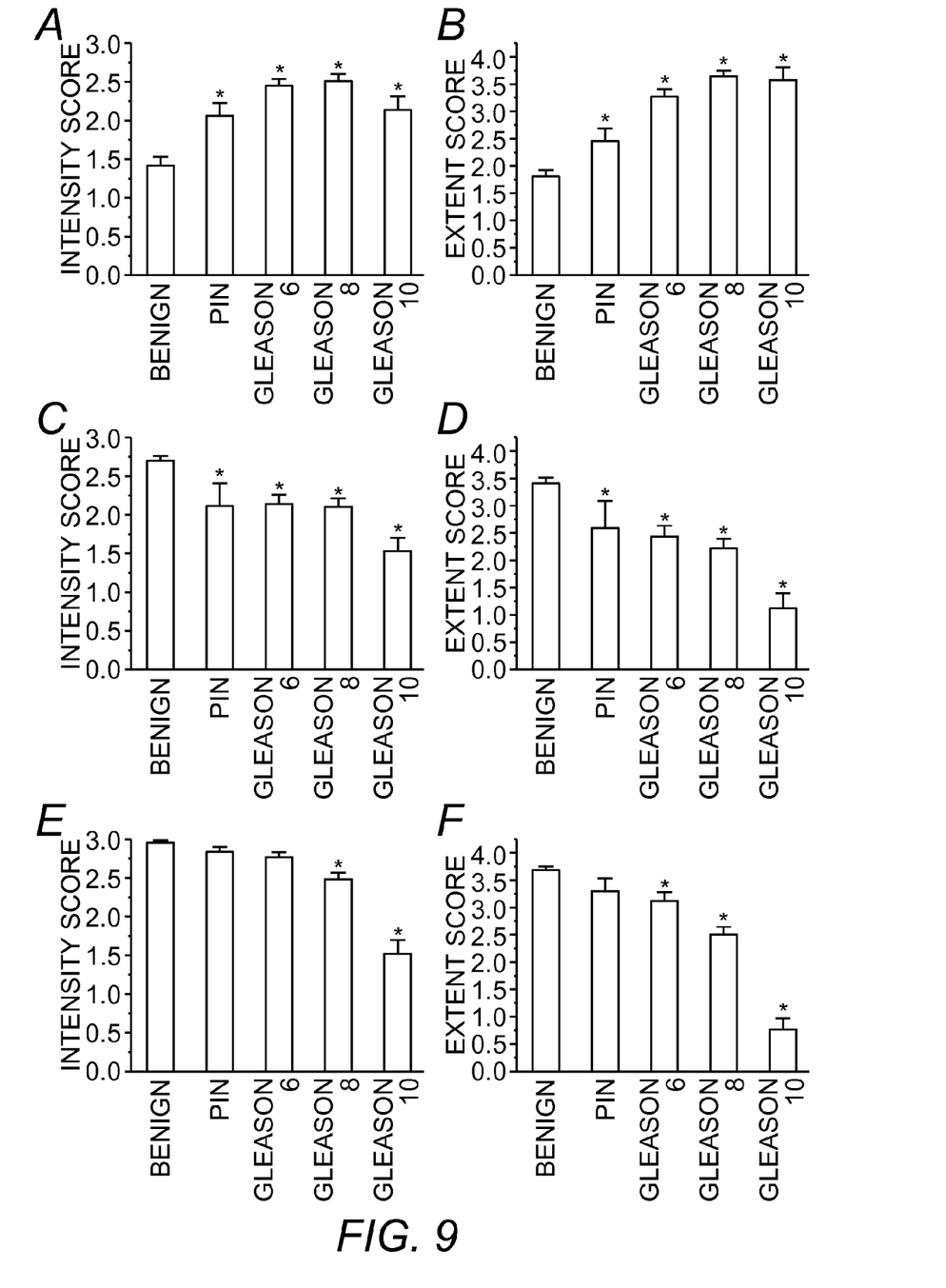
FIG. 9. Increased δ-catenin immunoreactivity is accompanied by the reduced E-cadherin and $p120^{ctn}$ immunostaining during prostate cancer progression. A and B. Correlation between the changes in the intensity (A) and extent (B) of δ-catenin immunoreactivity and the Gleason scored prostatic adenocarcinomas. C and D. Correlation between the changes in the intensity (C) and extent (D) of E-cadherin immunoreactivity and the Gleason scored prostatic adenocarcinomas. E and F. Correlation between the changes in the intensity (E) and extent (F) of $p120^{ctn}$ immunoreactivity and the Gleason scored prostatic adenocarcinomas, Asterisks: $p<0.05$

Interestingly, δ-catenin immunoreactivity increased significantly in high-grade prostate intraepithelial neoplasia (PIN), the most likely pre-invasive stage of prostatic adenocarcinomas. With increasing Gleason score, δ-catenin immunoreactivity continued to increase the intensity and extent until the prostatic adneocarcinoma reach Gleason score 10. At this stage, while the extent of δ-catenin staining remained the same, the intensity of δ-catenin staining decreased somewhat (FIGS. 9A and B). The E-cadherin and p120$^{ctn}$ immunoreactivities, on the other hand, showed a reciprocal trend in expression when compared with δ-catenin immunoreactivity (FIG. 9C-F). E-cadherin expression decreased significantly in PIN, but remained at the same level as in PIN in the tumors with Gleason scores 6 and 8. Then in Gleason 10 tumors, E-cadherin immunoreactivity reduced dramatically, reflecting the dispersion and the invasiveness of the tumor cells. The intensity of p120$^{ctn}$ expression did not go down significantly in PIN and Gleason 6 tumors. Even in the Gleason 8 tumors, the intensity and the extent of p120$^{ctn}$ immunoreactivity remained quite strong. However, in the Gleason 10 tumors, both the intensity and extent of p120$^{ctn}$ immunoreactivity reduced sharply (FIGS. 9E and F).

Increased δ-Catenin Expression is Accompanied by the Redistribution of E-Cadherin and p120$^{ctn}$ in the Same Tumor Clusters of Prostatic Adenocarcinomas.

One advantage of analyzing the serial sections of a single case is that all three cell-cell junction biomarkers in the same tumor cell clusters can be compared. In benign prostate glandular epithelial cells, δ-catenin immunoreactivity was quite weak (data not shown). Anti-E-cadherin immunoreactivities were strong and were concentrated at the cell-cell contact area, consistent with its localization to the adherens junction (data not shown). There was very little anti-E-cadherin immunoreactivity in the cytoplasm. Similarly, p120$^{ctn}$ immunoreactivity was clearly localized at the cell-cell junction (data not shown). In the low-grade prostatic adenocarcinomas (Gleason score 6), δ-catenin immunoreactivity was generally increased, and can be more evident in some cells than others in the same tumor clusters (data not shown). In some of these tumor clusters, the relationship among the immunoreactivities of δ-catenin, E-cadherin and p120$^{ctn}$ can be directly compared. For example, δ-catenin immunoreactivity was junctional in the central part of the tumor cluster. However, in the peripheral cell layer of the tumor cluster, not only the intensity of δ-catenin immunoreactivity was higher, but also most of the signal became non-junctional. When E-cadherin and p120$^{ctn}$ immunoreactivity were analyzed in the same tumor clusters, they showed strong junctional staining corresponding to the center of the cluster (data not shown), but became more cytoplasmic at the periphery of the tumor cluster (not shown). Nevertheless, the intensity and the extent of anti-E-cadherin and anti-p120$^{ctn}$ immunostaining did not reduce significantly in many of the low-grade prostatic adenocarcinomas. In the prostatic adenocarcinomas with high Gleason score of 10, cell-cell junctions were severely disrupted. Here, anti-δ-catenin immunoreactvity showed intense cytoplasmic staining (not shown). Most of the E-cadherin and p120$^{ctn}$ immunoreactivity at the cell-cell junction was either lost or redistributed to the cytoplasm (not shown).

Forced δ-Catenin Overexpression in CWR-R1 Derived from Human Prostate Cancer Xenograft Induces the Reduction of E-Cadherin and p120$_{ctn}$ at the Cell-Cell Junction.

Because δ-catenin binds to the same JMD region on E-cadherin as p120$^{ctn}$, an increased δ-catenin expression may compete with p120$^{ctn}$ for E-cadherin binding. As shown above, increased δ-catenin expression in prostatic adenocarcinomas indeed corresponded to the loss of E-cadherin and p120$^{ctn}$ at the cell-cell junction and their concomitant increases in cytoplasmic immunoreactivities (data not shown). To further examine the hypothesis that an increased δ-catenin expression can affect the E-cadherin and p120$^{ctn}$ at the cell-cell junction, we overexpressed δ-catenin ectopically into prostate epithelial cells in culture.

CWR-R1 cells (Gregory et al., Cancer Res. 61(7): 2892-2898, 2001) were derived from a recurrent human prostate cancer xenograft (Pretlow et al., supra 1993; Wainstein, M. A. et al., Cancer Res. 54 (23): 6049-6052, 1994). These cells grow in clusters in culture and displayed an enhanced δ-catenin immunoreactivity when compared with PZ-HPV-7, a non-tumorigenic human prostate epithelial cell line. The level of δ-catenin expression in CWR-R1 was moderate when compared with that in neurons (not shown). This moderate level of δ-catenin expression was also demonstrated in culture by immunofluorescent light microscopy. In the cell clusters, δ-catenin was localized at the cell-cell junction (not shown). In the same cell clusters, E-cadherin immunostaining corresponded mainly to the cell-cell contact area (not shown) and at least partially co-localized with δ-catenin at the cell-cell junction (not shown). When pEGFP-δ-catenin was overexpressed in CWR-R1 cells by transfection, its localization at the cell-cell junction was clearly demonstrated (not shown), along with some cytoplasmic immunoreactivity. Here, the purple line demarcated the untransfected cells in the field. When E-cadherin immunoreactivity was examined, the untransfected cells showed the same cell-cell junction staining. But the cells transfected with δ-catenin showed a reduced E-cadherin immunoreactivity (not shown). When the merged images were analyzed, no co-localization of E-cadherin and δ-catenin at the cell-cell junction area could be demonstrated.

We also examined the $p120^{ctn}$ immunoreactivity and distribution in the CWR-R1 cells transfected with pEGFP-δ-catenin. Untransfected cells showed $p120^{ctn}$ localization at the cell-cell junction (data not shown). However, cells transfected with δ-catenin showed the reduced $p120^{ctn}$ immunoreactivity (data not shown). In addition, $p120^{ctn}$ staining at the cell-cell junction was very weak, which was also shown by the lack of merged yellow staining at the cell-cell contact area (data not shown). As an additional control, CWR-R1 cells were transfected with EGFP vector alone, which uniformly distributed in the cytoplasm (data not shown). The untransfected cells were highlighted with the red lines (not shown). Here, anti-$p120^{ctn}$ immunoreactivity was localized to the cell-cell junction, whether in transfected or untransfected cells (not shown). The merged images showed strong red signals in most of the cells (not shown).

TABLE I

Paired analysis of δ-catenin immunoscores in benign versus prostate tumor sections.

| | Immunoscore | | |
|---|---|---|---|
| | Cancer > Benign | Cancer = Benign | Cancer < Benign |
| Number of Cases | 55/65 (85%) | 6/65 (9%) | 4/65 (6%) |

*Out of 90 cases, total 65 benign sections and 65 prostate tumor sections can be used for direct, paired comparison

TABLE II

Comparison of δ-catenin, E-cadherin and $p120^{ctn}$ immunoscores* in predicting prostate cancer.

| | Immunoscore | | | | | |
|---|---|---|---|---|---|---|
| | Benign | | | Cancer | | |
| Markers | Strong | Moderate | Weak | Strong | Moderate | Weak |
| δ-catenin | 10/65 (15%) | 6/65 (9%) | 49/65 (75%) | 46/72 (64%) | 20/72 (28%) | 6/72 (8%) |

TABLE II-continued

Comparison of δ-catenin, E-cadherin and $p120^{ctn}$ immunoscores* in predicting prostate cancer.

| | Immunoscore | | | | | |
|---|---|---|---|---|---|---|
| | Benign | | | Cancer | | |
| Markers | Strong | Moderate | Weak | Strong | Moderate | Weak |
| E-cadherin | 64/71 (90%) | 4/71 (6%) | 3/71 (4%) | 39/89 (44%) | 20/89 (22%) | 30/89 (34%) |
| $p120^{ctn}$ | 71/71 (100%) | 0/71 (0%) | 0/71 (0%) | 62/88 (70%) | 8/88 (9%) | 18/88 (21%) |

*Total 65 benign cases and 72 prostatic adenocarcinoma specimens stained with anti-δ-catenin, 71 benign cases and 89 prostatic adenocarcinoma specimens stained with anti-E-cadherin, and 71 benign cases and 88 prostatic adenocarcinoma samples stained with $p120^{ctn}$ can be used for direct comparison

TABLE III

The comparison of the ability of δ-catenin, E-cadherin and $p120^{ctn}$ immunoscores in correcting each other's false negative outcomes in predicting prostate cancer.

| Cases of false negative by one biomarker immunoreactivity: | δ-catenin correction | E-cadherin correction | $p120^{ctn}$ correction |
|---|---|---|---|
| δ-catenin (n = 6) | 0/6 (0%) | 4/6 (67%) | 5/6 (83%) |
| E-cadherin (n = 39) | 24/39 (62%) | 0/39 (0%) | 5/39 (13%) |
| $p120^{ctn}$ (n = 62) | 31/62 (50%) | 29/62 (47%) | 0/62 (0%) |

TABLE IV

Probability of successful prediction of prostate cancer using δ-catenin-E-cadherin-$p120^{ctn}$ immunoscore as a biomarker cluster.

| Cases of false negative by one biomarker immunoreactivity: | Successful correction using δ-catenin/E-cadherin/$p120^{ctn}$ |
|---|---|
| δ-catenin (n = 6) | 5/6 (83%) |
| E-cadherin (n = 39) | 24/39 (62%) |
| $p120^{ctn}$ (n = 62) | 49/62 (79%) |

The foregoing is illustrative of the present invention, and is not to be construed as limiting thereof. The invention is defined by the following claims with equivalents of the claims to be included therein.

That which is claimed is:

1. A method for detecting cancer in a subject comprising the steps of:
   obtaining a sample from an esophagus tissue of said subject;
   contacting said sample with anti-delta-catenin antibodies selected from the group consisting of mAbD30, rAb62, rAb64 and rAb25 to form an anti-delta-catenin antigen complex; and
   detecting the presence of anti-delta-catenin antigen complex,
   wherein the presence of antigen-antibody complex indicates the presence of cancer, wherein said cancer is esophageal cancer, and wherein said delta-catenin is also known as the adherens-junction linked arm (ALARM) protein.

2. The method of claim 1, wherein said subject is a human.

3. The method of claim 1, wherein said subject is male.

4. The method of claim 1, wherein said subject is female.

5. The method of claim 1, wherein the sample is a tissue sample, cell sample or stroma sample.

6. The method of claim 5, wherein an intervening culturing step is performed between the time the cell sample is obtained from the subject and an immunoassay is carried out on the cell sample.

7. The method of claim 1, wherein the anti-delta-catenin antibody is mAbD30.

8. The method of claim 1, wherein the anti-delta-catenin antibody is rAb62.

9. The method of claim 1, wherein the anti-delta-catenin antibody is rAb64.

10. The method of claim 1, wherein the anti-delta-catenin antibody is rAb25.

11. The method of claim 1 further comprising measuring the amount of anti-delta-catenin antigen complex,
    wherein elevated levels of antigen-antibody complex indicates the presence of cancer, with greater levels of antigen-antibody complex indicating greater severity or progression of said cancer.

12. The method of claim 1 further comprising contacting said sample with delta-catenin specific primers to form a delta-catenin PCR reaction product; and
    detecting the presence of delta-catenin PCR reaction product,
    wherein the presence of delta-catenin PCR product indicates the presence of cancer.

13. The method of claim 1 further comprising contacting said sample with delta-catenin specific primers to form a delta-catenin PCR reaction product; and
    measuring the amount of delta-catenin PCR reaction product,
    wherein elevated levels of delta-catenin PCR reaction product indicates the presence of cancer, with greater levels of delta-catenin PCR reaction product indicating greater severity or progression of said cancer.

14. A method for detecting esophageal cancer in a subject comprising:
    contacting a tissue sample from an esophagus of the subject with anti-delta-catenin antibodies selected from the group consisting of mAbD30, rAb62, rAb64 and rAb25 to form an anti-delta-catenin antigen complex; and
    measuring the distribution of anti-delta-catenin antigen complex in a cell-cell junction and the cytoplasm, wherein greater levels of antigen-antibody complex in the cytoplasm compared to the cell-cell junction represents a redistribution of the anti-delta-catenin antigen complex indicating a greater severity or progression of the esophageal cancer.

15. The method of claim 14, wherein the anti-delta-catenin antibody is mAbD30.

16. The method of claim 14, wherein the anti-delta-catenin antibody is rAb62.

17. The method of claim 14, wherein the anti-delta-catenin antibody is rAb64.

18. The method of claim 14, wherein the anti-delta-catenin antibody is rAb25.

* * * * *